United States Patent [19]

O'Lenick, Jr.

[11] Patent Number: 5,760,260
[45] Date of Patent: Jun. 2, 1998

[54] MEADOWFOAM ESTERS

[75] Inventor: Anthony J. O'Lenick, Jr., Lilburn, Ga.

[73] Assignee: Fan Tech Ltd., Chicago, Ill.

[21] Appl. No.: 759,266

[22] Filed: Dec. 2, 1996

Related U.S. Application Data

[63] Continuation-in-part of Ser. No. 516,138, Aug. 17, 1995, Pat. No. 5,646,321.

[51] Int. Cl.$^6$ .................................................. C07C 37/02
[52] U.S. Cl. ........................................ 554/224; 554/223
[58] Field of Search ................................ 589/224, 223

[56] References Cited

U.S. PATENT DOCUMENTS 4,425,458  1/1984  Lindner et al. ......................... 524/314
4,868,236  9/1989  O'Lenick ............................... 524/308

OTHER PUBLICATIONS

Miwa et al., JAOCS, pp. 724–744, 1963.
Morrison & Boyd, Organic Chemistry, 4th ed., p. 828, 1983.

*Primary Examiner*—Gary Geist
*Assistant Examiner*—Deborah D. Carr

[57] ABSTRACT

The present invention deals with the certain novel esters which are prepared by the reaction of an alcohol and meadowfoam fatty, methyl ester or triglyceride. These materials are useful as cosmetic ingredients where outstanding liquidity, resistance to oxidation, and minimal taste and odor variation are required. This combination of properties make these compounds excellent candidates as additives to personal care products like skin care oils and lipsticks.

9 Claims, No Drawings

MEADOWFOAM ESTERS

BACKGROUND OF THE INVENTION

Related Applications

This application is a continuation in part of application Ser. No. 08/516,138 filed Aug. 17, 1995, now U.S. Pat. No. 5,646,321.

1. Field of the Invention

The present invention deals with the certain esters which are prepared by the reaction of an alcohol and meadowfoam fatty, methyl ester or triglyceride. These materials are useful as cosmetic ingredients where outstanding liquidity, resistance to oxidation, and minimal taste and odor variation are required. This combination of properties make these compounds excellent candidates as additives to personal care products like skin care oils and lipsticks.

2. Description of the Art Practices

Liquid esters have been made using guerbet alcohols. This application is a continuation in part of an application which discloses guerbet derivatives of meadowfoam. We have also surprisingly discovered that esters made using linear fatty alcohols also have good liquidity and good oxidative stability.

U.S. Pat. No. 4,868,236 to O'Lenick discloses a guerbet citric ester and polymers thereof useful in plastic lubrication.

U.S. Pat. No. 4,425,458 to Lindner and O'Lenick teaches that specific guerbet esters can be used as polycarbonate lubricants.

There are many applications in which liquid esters are desired. One of the ways in which a liquid ester can be made is to incorporate unsaturated groups into the molecule. Selecting unsaturated acids, like oleic acid, however results in an ester which undergoes a degradation process referred to as "rancidity". This makes them unacceptable for applications where odor and taste is an issue. The recent availability of meadowfoam oil, with it's 20 to 22 carbon atoms and the specific location of it's double bonds, and it's reaction with fatty alcohols results in liquid stable ester, acceptable for use in pigmented personal care applications, like make-up and lipstick.

None of the prior compounds possess the critical meadowfoam carboxy moiety. Molecules of the current invention have the meadowfoam alkyl group in the acid portion of the molecule.

THE INVENTION

This invention relates to a particular group of meadowfoam esters based upon meadowfoam oil, meadowfoam methyl ester or meadowfoam fatty acid. The terms meadowfoam oil, fatty acid or methyl ester as used herein refer to a specific alkyl distribution of the groups which is are native to a plant limnathes Alba, commonly called meadowfoam oil. Meadowfoam oil is harvested from a plant and sold commercially by The Fanning Corporation under the tradename "Fancor Meadowfoam". The unique structure of the oil allows for the synthesis of esters which are liquid and exhibit a high degree of oxidative stability heretofore unattainable. The fatty distribution of the oil ranges from 20 to 22 carbons and has unsaturation in specific locations. The oil contains 97% by weight higher unsaturated alkyl groups. Typically, meadowfoam oil contains 60–65% of a twenty carbon mono-carboxy acid having one unsaturation between carbon 5 and 6. Additionally, it contains 12–20% of a twenty two carbon mono-carboxy acid having one unsaturation between either carbon 5 and 6, or carbon 13 and 14 and 15–28% of a twenty two carbon mono-carboxy acid having one unsaturation between both carbon 5 and 6, or carbon 13 and 14. The combination of the fact that there are 20 to 22 carbon atoms in the group leads to lack of volatility, the presence of unsaturation leads to liquidity and the fact that the di-unsaturated moieties are not conjugated leads to outstanding oxidative stability.

Additional aspects of the invention is the application of these materials as personal care applications were the specific properties of an ester derived the unique distribution of the meadowfoam on the other result in superior liquidity, lubricity, and outstanding oxidative stability.

The compounds of the current invention are meadowfoam esters conforming to the following structure;

wherein:

R is

60–65% by weight

12–20% by weight a mixture of

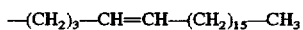

and

and

15–28% by weight

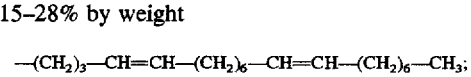

a is an integer ranging from 6 to 28.

Preferred Embodiment

In a preferred embodiment a is 6.

In another preferred embodiment a is 8.

In another preferred embodiment a is 10.

In still another preferred embodiment a is 12.

In another preferred embodiment a is 14.

In still another preferred embodiment a is 16.

In another preferred embodiment a is 18.

In another preferred embodiment a is 28.

The invention also teaches that an ester can be made by the esterification reaction of an alcohol conforming to the following structure;

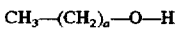

a is an integer ranging from 6 to 28, and meadowfoam oil.

In a preferred embodiment the esterification is conducted at a temperature of between 150 and 210 C.

In another preferred embodiment the esterification is conducted using methane sulfonic acid as a catalyst.

EXAMPLES

Raw Materials

Alcohols

Fatty alcohols are well known to those skilled in the art. They are sold by a variety of manufacturers including Condea Vista.

| Example | Common Name | a |
|---|---|---|
| 1 | n-octanol | 6 |
| 2 | n-decanol | 8 |
| 3 | n-tetradecanol | 12 |
| 4 | n-octadecanol | 16 |
| 5 | n-docosanol | 20 |
| 6 | n-tetracosanol | 22 |
| 7 | n-tricontanol | 28 |

Meadowfoam Oil

Meadowfoam Oil can be used as a triglyceride, which is the oil as provided, reacted with methanol in processes known to those skilled in the art to make methyl ester, or reacted using technology known in the art to make carboxylic acids. The CAS number of meadowfoam oil is 153065-40-8.

The choice of triglyceride, acid or methyl ester does not change the structure of the resultant ester. It does however change the by-product produced. In the case of the triglyceride, glycerine is produced, in the case of the acid water is produced and in the case of the methyl ester methanol is produced.

Ester Synthesis

The esterification reaction is carried out using an excess of alcohol or meadowfoam or more typically using an equivalent of each. The esterification reaction can be carried out with or without catalyst, however when no catalyst is used the reaction times are protracted. Catalysts like benzene sulfonic acid, tin, sulfuric acid, tin salts and the like can be used. The most satisfactory catalyst is stannous oxylate.

General Procedure—Meadowfoam Oil

To the specified number of grams of alcohol (examples 1–7) is added then 354.0 grams of the meadowfoam oil. Next add 0.1% stannous oxylate based upon the total weight of the batch after all ingredients have been charged, under agitation. The temperature of the mass is raised to 150–200 C. and glycerine is stripped off under vacuum. The acid value and hydroxyl value drop to vanishingly small values, and the saponification value increases to theoretical.

The products are clear liquids and are liquid to extraordinary temperatures. They exhibit outstanding lubrication properties and are outstanding viscosity index modifiers.

| | Alcohol | |
|---|---|---|
| Example | Example | Grams |
| 8 | 1 | 130.0 |
| 9 | 2 | 158.0 |
| 10 | 3 | 214.4 |
| 11 | 4 | 270.5 |
| 12 | 5 | 326.6 |
| 13 | 6 | 354.6 |
| 14 | 7 | 438.8 |

General Procedure—Meadowfoam Oil

To the specified number of grams of alcohol (examples 1–7) is added then 354.0 grams of the meadowfoam fatty acid. Next add 0.1% stannous oxylate based upon the total weight of the batch after all ingredients have been charged, under agitation. The temperature of the mass is raised to 180–200 C. and water is stripped off under vacuum. The acid value and hydroxyl value drop to vanishingly small values, and the saponification value increases to theoretical.

The products are clear liquids and are liquid to extraordinary temperatures. They exhibit outstanding lubrication properties and are outstanding viscosity index modifiers.

| | Alcohol | |
|---|---|---|
| Example | Example | Grams |
| 15 | 1 | 130.0 |
| 16 | 2 | 158.0 |
| 17 | 3 | 214.4 |
| 18 | 4 | 270.5 |
| 19 | 5 | 326.6 |
| 20 | 6 | 354.6 |
| 21 | 7 | 438.8 |

Liquid products which contain unsaturation are subject to an oxidation process referred to as rancidity. The double bond (conjugated or unconjugated) present for the desired liquidity is oxidized to aldehydes and ketones which react to form compounds causing bad color, odor and taste. In many applications including lipsticks, mal odor and mal taste are major problems, but liquidity and hydrophobicity and liquidity are desired. The presence of the aldehydic rancidity by-products produce unacceptable odor, color and taste components have a profound effect upon these properties at very minute concentrations. Studies have shown that the part per billion levels of some aldehydic compounds cause unacceptable properties.

Rancidity Testing

Rancidity was tested using gas chromatography on the head space above the product stored at specific conditions looking for degradation products.

(Addition of 5 grams product to be tested to a 100 ml bottle equipped with a rubber septum top stored for 3 months)

| Material | Aldehyde (Head Space analysis) | Odor | Taste |
|---|---|---|---|
| Temperature: 20 C. | | | |
| Example 4 | None Detected | Good | Good |
| Example 7 | None Detected | Good | Good |
| Example 6 | None Detected | Good | Good |
| Unsaturated Compounds | | | |
| Oleic acid - Guerbet 20 Ester | 80 ppm | Fair | Fair |
| Oleic Acid Guerbet 16 ester | 100 ppm | Unacceptable | Fair |
| Tridecyl Oleate | 90 ppm | Fair | Fair |
| TMP Trioleate | 120 ppm | Unacceptable | Unacceptable |
| Material | Aldehyde (Head Space) | Odor | Taste |
| Temperature: 50 C. | | | |
| Example 4 | None Detected | Good | Good |
| Example 7 | None Detected | Good | Good |
| Example 6 | None Detected | Good | Good |
| Material | Aldehyde (Head Space analysis) | Odor | Taste |
| Unsaturated Compounds | | | |
| oleic acid C-20 Guerbet ester | 200 ppm | Unacceptable | Unacceptable |

| | | | |
|---|---|---|---|
| Oleic Acid C-16 Guerbet ester | 175 ppm | Unacceptable | Fair |
| Tridecyl Oleate | 220 ppm | Unacceptable | Unacceptable |
| TMP Trioleate | 210 ppm | Unacceptable | Unacceptable |

Oleic Acid/C-20 Guerbet ester is the reaction product of (Raw material example 6) and oleic acid.

Oleic Acid/C-16 Guerbet ester is the reaction product of (Raw material example 4) and oleic acid.

Tmp trioleate is trimethylol propane tri oleate and is an item of commerce.

I claim:

1. A meadowfoam ester conforming to the following structure;

CH₃—(CH₂)ₐ—O—C(O)—R wherein

R is

60–65% by weight

—(CH₂)₃—CH=CH—(CH₂)₁₃—CH₃

12–20% by weight a mixture of

—(CH₂)₃—CH=CH—(CH₂)₁₅—CH₃ and

—(CH₂)₁₁—CH=CH—(CH₂)₇—CH₃ and

15–28% by weight

—(CH₂)₃—CH=CH—(CH₂)₆—CH=CH—(CH₂)₆—CH₃;

a is an integer ranging from, 6 to 28.

2. A meadowfoam ester of claim 1 wherein a is 6.
3. A meadowfoam ester of claim 1 wherein a is 8.
4. A meadowfoam ester of claim 1 wherein a is 10.
5. A meadowfoam ester of claim 1 wherein a is 12.
6. A meadowfoam ester of claim 1 wherein a is 14.
7. A meadowfoam ester of claim 1 wherein a is 16.
8. A meadowfoam ester of claim 1 wherein a is 18.
9. A meadowfoam ester of claim 1 wherein a is 20.

* * * * *